US011072593B2

(12) United States Patent
Gebhardt et al.

(10) Patent No.: US 11,072,593 B2
(45) Date of Patent: Jul. 27, 2021

(54) PROCESS FOR THE EPOXIDATION OF A TETRASUBSTITUTED ALKENE

(71) Applicant: BASF Agro B.V., Arnhem (NL)

(72) Inventors: Joachim Gebhardt, Ludwigshafen (DE); Michael Rack, Ludwigshafen (DE); Bernd Wolf, Ludwigshafen (DE); Stefan Benson, Ludwigshafen (DE); Roland Goetz, Ludwigshafen (DE); Helmut Kraus, Research Triangle Park, NC (US)

(73) Assignee: BASF AGRO B.V., Arnhem (NL)

( * ) Notice: Subject to any disclaimer, the term of this patent is extended or adjusted under 35 U.S.C. 154(b) by 193 days.

(21) Appl. No.: 16/309,478

(22) PCT Filed: Jun. 1, 2017

(86) PCT No.: PCT/EP2017/063276
§ 371 (c)(1),
(2) Date: Dec. 13, 2018

(87) PCT Pub. No.: WO2017/215928
PCT Pub. Date: Dec. 21, 2017

(65) Prior Publication Data
US 2020/0308125 A1    Oct. 1, 2020

(30) Foreign Application Priority Data
Jun. 15, 2016 (EP) .................................. 16174601

(51) Int. Cl.
| *C07D 301/16* | (2006.01) |
| *C07D 303/04* | (2006.01) |
| *C07D 493/08* | (2006.01) |
| *B01J 19/00*  | (2006.01) |

(52) U.S. Cl.
CPC ......... *C07D 301/16* (2013.01); *C07D 303/04* (2013.01); *C07D 493/08* (2013.01); *B01J 19/0086* (2013.01)

(58) Field of Classification Search
CPC .. C07D 301/16; C07D 303/04; C07D 493/08; B01J 19/0086
See application file for complete search history.

(56) References Cited

U.S. PATENT DOCUMENTS

| 3,130,207 A | 4/1964 | Greenspan et al. |
| 3,676,504 A | 7/1972 | Leffingwell |
| 4,257,948 A | 3/1981 | Costerousse et al. |
| 4,487,945 A | 12/1984 | Payne |
| 4,542,244 A | 9/1985 | Payne et al. |
| 4,898,954 A | 2/1990 | Mohrmann et al. |
| 4,945,100 A | 7/1990 | Nyfeler et al. |
| 4,992,458 A | 2/1991 | Riebli et al. |
| 5,143,932 A | 9/1992 | Jautelat et al. |
| 6,229,028 B1 | 5/2001 | Neumann et al. |

FOREIGN PATENT DOCUMENTS

| CA | 1171866 A | 7/1984 |
| CA | 1209152 A | 8/1986 |
| CN | 1467029 A | 1/2004 |
| CN | 101602770 A | 12/2009 |
| DE | 1003180 B | 2/1957 |
| DE | 3042302 A1 | 8/1981 |
| DE | 3315681 A1 | 10/1984 |
| DE | 3733755 A1 | 4/1989 |
| EP | 0032990 A1 | 8/1981 |
| EP | 0081893 A2 | 6/1983 |
| EP | 0735142 B1 | 10/2001 |
| EP | 2192118 A1 | 6/2010 |
| EP | 3126430 A1 | 2/2017 |
| EP | 3275955 A1 | 1/2018 |
| EP | 3298020 A1 | 3/2018 |
| EP | 3081893 B1 | 12/2018 |
| EP | 3113640 B1 | 2/2019 |
| GB | 1307053 A | 2/1973 |
| JP | H10248541 A | 9/1998 |
| WO | 2002085891 A1 | 10/2002 |
| WO | 2006128126 A1 | 11/2006 |
| WO | 2009115490 A2 | 9/2009 |
| WO | 2010145992 A1 | 12/2010 |
| WO | 2012080239 A1 | 6/2012 |
| WO | 2013007767 A1 | 1/2013 |
| WO | 2013010862 A1 | 1/2013 |
| WO | 2013066360 A1 | 5/2013 |
| WO | 2013124791 A1 | 8/2013 |
| WO | 2013189910 A1 | 12/2013 |
| WO | 2014012811 A1 | 1/2014 |

(Continued)

OTHER PUBLICATIONS

European Search Report for EP Patent Application No. 16174601.1, dated Sep. 12, 2016, 4 pages.
International Search Report for PCT Application No. PCT/EP2017/063276, dated Jul. 5, 2017, 4 pages.
Gan, et al., "Kinetic Studies of the Performic Acid Epoxidation of Natural Rubber Latex Stabilized by Cationic Surfactant", European Polymer Journal, vol. 22, Issue 7, 1986, pp. 573-576.
Gnecco, et al., "Epoxidation of Low-Molecular-Weight Euphorbia Lactiflua Natural Rubber With "In Situ" Formed Performic Acid", Polymer Bulletin, vol. 37, Issue 5, 1996, pp. 609-615.
Galemmo, JR., et al., "Contrasting Directed-Aldol Reactivity of a Pair of Epimeric Trimethylsilyl Enol Ethers", The Journal of Organic Chemistry, vol. 50, Issue 10, 1985, pp. 1768-1770.

(Continued)

*Primary Examiner* — Timothy R Rozof
(74) *Attorney, Agent, or Firm* — Marshall, Gerstein & Borun LLP

(57) ABSTRACT

This invention relates to a process for the epoxidation of a tetrasubstituted alkene such as terpinolene to the corresponding epoxide such as terpinolene epoxide by reacting the tetrasubstituted alkene with performic acid prepared in situ from formic acid and hydrogen peroxide in the presence of at least one buffering agent. Further, the invention relates to the use of an oxidizing agent comprising hydrogen peroxide and formic acid for the in-situ epoxidation of a tetrasubstituted alkene.

12 Claims, No Drawings

(56) References Cited

FOREIGN PATENT DOCUMENTS

| | | |
|---|---|---|
| WO | 2014026845 A1 | 2/2014 |
| WO | 2014026893 A1 | 2/2014 |
| WO | 2014026928 A1 | 2/2014 |
| WO | 2014060449 A1 | 4/2014 |
| WO | 2014108286 A1 | 7/2014 |
| WO | 2014111398 A1 | 7/2014 |
| WO | 2014135392 A1 | 9/2014 |
| WO | 2014155214 A1 | 10/2014 |
| WO | 2014184014 A1 | 11/2014 |
| WO | 2014184015 A1 | 11/2014 |
| WO | 2014184016 A1 | 11/2014 |
| WO | 2014184017 A1 | 11/2014 |
| WO | 2014184019 A1 | 11/2014 |
| WO | 2014184073 A1 | 11/2014 |
| WO | 2014184074 A1 | 11/2014 |
| WO | 2014187705 A1 | 11/2014 |
| WO | 2014202589 A1 | 12/2014 |
| WO | 2015003858 A1 | 1/2015 |
| WO | 2015007564 A1 | 1/2015 |
| WO | 2015011119 A2 | 1/2015 |
| WO | 2015011120 A2 | 1/2015 |
| WO | 2015022634 A2 | 2/2015 |
| WO | 2015022636 A2 | 2/2015 |
| WO | 2015022639 A2 | 2/2015 |
| WO | 2015049160 A1 | 4/2015 |
| WO | 2015049360 A1 | 4/2015 |
| WO | 2015052152 A1 | 4/2015 |
| WO | 2015052153 A1 | 4/2015 |
| WO | 2015052173 A1 | 4/2015 |
| WO | 2015052178 A1 | 4/2015 |
| WO | 2015055447 A1 | 4/2015 |
| WO | 2015067494 A1 | 5/2015 |
| WO | 2015075087 A1 | 5/2015 |
| WO | 2015082415 A1 | 6/2015 |
| WO | 2015082422 A2 | 6/2015 |
| WO | 2015086596 A1 | 6/2015 |
| WO | 2015086698 A1 | 6/2015 |
| WO | 2015091045 A1 | 6/2015 |
| WO | 2015124651 A1 | 8/2015 |
| WO | 2015155236 A1 | 10/2015 |
| WO | 2015158518 A1 | 10/2015 |
| WO | 2015158565 A1 | 10/2015 |
| WO | 2015169883 A1 | 11/2015 |
| WO | 2016001025 A1 | 1/2016 |
| WO | 2016005211 A1 | 1/2016 |
| WO | 2016016369 A1 | 2/2016 |
| WO | 2016037785 A1 | 3/2016 |
| WO | 2016055404 A1 | 4/2016 |
| WO | 2016062814 A1 | 4/2016 |
| WO | 2016071243 A1 | 5/2016 |
| WO | 2016180614 A1 | 11/2016 |
| WO | 2016180642 A1 | 11/2016 |
| WO | 2016180833 A1 | 11/2016 |
| WO | 2016202807 A1 | 12/2016 |
| WO | 2017009054 A1 | 1/2017 |
| WO | 2017009056 A1 | 1/2017 |
| WO | 2017009061 A1 | 1/2017 |
| WO | 2017009088 A1 | 1/2017 |
| WO | 2017009089 A1 | 1/2017 |
| WO | 2017009090 A1 | 1/2017 |
| WO | 2017009092 A1 | 1/2017 |
| WO | 2017009095 A1 | 1/2017 |
| WO | 2017009124 A1 | 1/2017 |
| WO | 2017009134 A1 | 1/2017 |
| WO | 2017009137 A1 | 1/2017 |
| WO | 2017009138 A1 | 1/2017 |
| WO | 2017009139 A1 | 1/2017 |
| WO | 2017009140 A1 | 1/2017 |
| WO | 2017009142 A1 | 1/2017 |
| WO | 2017009143 A1 | 1/2017 |
| WO | 2017009144 A1 | 1/2017 |
| WO | 2017009145 A1 | 1/2017 |
| WO | 2017009146 A1 | 1/2017 |
| WO | 2017009147 A1 | 1/2017 |
| WO | 2017009148 A1 | 1/2017 |
| WO | 2017012938 A1 | 1/2017 |
| WO | 2017102905 A1 | 6/2017 |
| WO | 2017133942 A1 | 8/2017 |
| WO | 2017144336 A1 | 8/2017 |
| WO | 2017144337 A1 | 8/2017 |
| WO | 2017215928 A1 | 12/2017 |
| WO | 2017215929 A1 | 12/2017 |

OTHER PUBLICATIONS

Patra, et al., "A Simple and Efficient Method for the Epoxidation of α,β-Unsaturated Aldehydes and Ketones Using Aqueous Hydrogen Peroxide-Sodium Ethoxide", Organic Preparations and Procedures International, vol. 35, Issue 5, 2003, pp. 515-520.

Pansevch-Kolyada et al. "Preparation of Peracetic Acid", Vestsi Akademii Navuk BSSR, Seryya Khimichnykb, 1973, vol. 6, p. 109-110 (Abstract).

Office Action dated Jul. 5, 2019, from U.S. Appl. No. 16/309,475, filed Dec. 13, 2018.

Afon'kin et al., "Synthesis of Some Electron-Rich Aryl(hetaryl)oxiranes under Phase-Transfer and Homogeneous Conditions," Russian Journal of Organic Chemistry, vol. 44, No. 12, (2008), pp. 1776-1779.

Aldrich, "Handbook of Fine Chemicals" 1998-1999, p. 367 and 1645-1646.

Brandes and Jacobsen, "Synthesis of Enantiopure 3-chlorostyrene Oxide via an Asymmetric Epoxidation-Hydrolytic Kinetic Resolution Sequence," Tetrahedron:Asymmetry, vol. 8, No. 23, (1997), pp. 3927-3933.

Cooper, et al., "Oxidation Reactions Using Urea-Hydrogen Peroxide; A Safe Alternative to Anhydrous Hydrogen Peroxide", Synlett, vol. 1990, Issue 9, Sep. 1, 1990, pp. 533-535.

Corey and Chaykovsky, "Dimethyloxosulfonium Methylide ((CH3)2SOCH2) and Dimethylsulfonium Methylide (CH3)2SCH2). Formation and Application to Organic Synthesis," Journal of American Chemical Society, vol. 87, No. 3, (1965), pp. 1353-1364.

Forrester et al., "Generation of Trimethylsulfonium Cation from Dimethyl Sulfoxide and Dimethyl Sulfate: Implications for the Synthesis of Epoxides from Aldehydes and Ketones," J. Chem. Soc. Perkin Trans. (1995), pp. 2289-2291.

Gurudutt et al., "Acid-Catalysed Rearrangement of Terpinolene Oxide," Indian Journal of Chemistry, Section B, Council of Scientific and Industrial Research, vol. 24B, (1985), pp. 820-823.

Kasyan, et al., "Azabrendanes. III. Synthesis of stereoisomeric exo and endo5acylaminomethylexo2,3epoxybicyclo :22.1]heptanes and their reduction by lithium aluminum hydride", Heteroatom Chemistry, vol. 12, Issue 3, 2001, pp. 119-130.

Kas'Yan, et aL, "Derivatives of exo-5-Aminomethyl-endo-5-methylbicyclo[2.2.1]hept-2-ene and exo-5-Aminomethyl-ando-5-methyl-exo-2,3-epoxybicyclo[2.2.1]heptane", Russian Journal of Organic Chemistry, vol. 37, Issue 11, 2001, 3p. 1564-1569.

Kas'Yan, et al_, "Amides containing two norbomene fragments_ Synthesis and chemical transformations", Russian Journal of Organic Chemistry, vol. 40, Issue 10, Oct. 2004, pp. 1415-1426.

Kasyan, et al_., "Azabrendanes IV_ Synthesis and characterization of N-(alkyl- and benzylsulfonyl)-exo-2-hydroxy-4-3zatricyclo[4.2.1.03,7]nonanes", Tetrahedron, vol. 63, Issue 8, Feb. 19, 2007, pp. 1790-1797.

Kas'Yan, et al_, "Stereoisomeric N-(p-Nitrobenzoyl)-5-aminomethylbicyclo[2.2.1]hept-2-enes_ Synthesis, Epoxidation, 1H and 13C NMR Spectra", Russian Journal of Organic Chemistry, vol. 38, Issue 2, Feb. 2002, pp. 165-175.

Kaur, et al., "Epoxidation Studies of Terpenes with Urea Hydrogen Peroxide and Phosphotungstic Acid", Indian Journal of Chemistry, vol. 49B, Issue 5, May 2010, pp. 598-602.

Kleschick, et al., "The Synthesis of Conformationally Restricted Analogs of Acetolactate", Synthesis, vol. 1997, Issue 7, Jul. 1, 1997, pp. 783-786.

Kuzenkov, "Synthesis of Substituted 2-azolyl-1-pyridylethan-1-ols," Chemistry of Heterocyclic Compounds, vol. 39, No. 11, (2003), pp. 1492-1495_.

(56) References Cited

OTHER PUBLICATIONS

Mosset and Gree, "Trimethylsulfonium Methylsulfate, a Simple and Efficient Epoxidizing Agent," Synthetic Communications, vol. 15, No. 8, (1985), pp. 749-757.

Schoenauer, et al., Structure-Odor Activity Studies on Monoterpenoid Mercaptans Synthesized by Changing the Structural Motifs of the Key Food Odorant 1-p-Menthene-8-thior, Journal of Agricultural and Food Chemistry, vol. 64, Issue 19, May 18, 2016, pp. 3849-3861.

Uguina et al., "Alumina as Heterogeneous Catalyst for the Regioselective Epoxidation of Terpenic Diolefins with Hydrogen Peroxide," Journal of Molecular Catalysis A: Chemical, 2006, vol. 256, pp. 208-215_.

Van Vliet et al., "Hexafluoroacetone in Hexafluoro-2-propanol: A Highly Active Medium for Epoxidation with Aqueous Hydrogen Peroxide," Synlett, No. 8, (2001), pp. 1305-1307_.

Yu et al., Synthesis and Fungicidal Evaluation of 2-Arylphenyl Ether-3-(11-1-1,2,4-triazol-1-y0propan-2-ol Derivatives, J. Agric_ Food Chem., vol. 57, No. 11, (2009), pp. 4854-4860.

Jankovic, et al., "The epoxidation of linseed oil with in situ formed peracetic acid: a model with included influence of the oil fatty acid composition", Industrial Crops and Products, vol. 143, Jan. 2020, p. 111881(1-11).

Kaur, et al., "Peroxy Acids: Role in Organic Synthesis", Synthetic Communications, vol. 44, Issue 6, Feb. 20, 2014, pp. 721-747.

Kurti, et al., "Prilezhaev Reaction", Strategic Applications of Named Reactions in Organic Synthesis, Mar. 4, 2005, 5 pages.

W.R. Sanderson, "Chapter 9: Hydrogen peroxide in clean processes", Chemistry of Waste Minimization, 1st Edition, Ed. James H. Clark, 1995, pp. 247-327.

PROCESS FOR THE EPOXIDATION OF A TETRASUBSTITUTED ALKENE

This application is a National Stage application of International Application No. PCT/EP2017/063276, filed Jun. 1, 2017. This application also claims priority under 35 U.S.C. § 119 to European Patent Application No. 16174601.1, filed Jun. 15, 2016.

This invention relates to a process for the epoxidation of a tetrasubstituted alkene such as terpinolene of the formula (Ia) to the corresponding epoxide such as terpinolene epoxide of the formula (IIa).

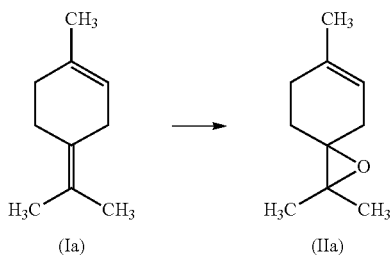

Because of its wide utility, the epoxidation of alkenes is important on an industrial scale. Tetrasubtituted olefins are common structural units in many classes of compounds, particularly natural products. Their corresponding epoxides are useful as intermediates for producing compounds used in various final applications such as in the pharmaceutical, agricultural and fine chemical industries.

For example, terpinolene epoxide is a valuable intermediate in the synthesis of terpinene-4-ol—an unsaturated tertiary terpene alcohol that occurs naturally in a number of essential oils. Terpinene-4-ol finds use as a component in synthetic essential oils which are compounded for use as flavors or perfumes. Because of high costs and uncertainty of supply of the natural product, synthetic routes to terpinene-4-ol have been developed, e.g. via epoxidation route starting from epoxidation of terpinolene. Nevertheless, there is still room for improvement with regard to the epoxidation step.

U.S. Pat. No. 3,676,504 describes a process for the preparation of terpinolene epoxide by epoxidation of terpinolene by using an organic peroxy acid, such as peracetic, perpropionic or m-chloroperbenzoic acid as oxidizing agents. The exemplified epoxidation of terpinolene makes use of a preformed 40% solution of peracetic acid as oxidizing agent.

Similarly, preformed peracetic acid (38%) is used for the epoxidation of the isopropylidene double bond in (3R*, 3aS*,7aS*)-Tetrahydro-5-isopropylidene-3,7,7-trimethyl-4 (3aH)-indanone as described in Robert A. Galemno et al, Journal of Organic Chemistry, Vol. 50, pages 1768-1770, 1985.

It is known that some of the preformed, in particular highly concentrated peroxy acid solutions are unstable, and cannot be safely stored or handled. Since peroxy acids can decompose spontaneously under explosion due to thermal or mechanical stress and their reactions are often highly exothermic, specific safety measures such as e.g. proper cooling and dilution are required during the course of the reaction. This leads to a low space-time yield and makes such reactions not very suitable for an industrial scale preparation. Further, the peroxy acids used in this process are relatively expensive and lead to a relatively high loading of organic matter in the production wastewater. The reaction is effected in a halogenated organic solvent (i.e. methylene chloride). However, the use of such halogenated solvents has the disadvantage that the production wastewaters contain hazardous AOX (absorbable organic halogen compounds) which is undesirable from an environmental point of view.

EP 0032990 A1 describes the conversion of specific olefinically unsaturated compounds into the corresponding epoxides by reaction with performic acid formed in situ. The exemplified alkenes are not more than trisubstituted. This process requires that a high concentration of an inorganic salt which is inert and neutral under the reaction conditions (e.g. sodium sulfate, sodium chloride or potassium chloride) is maintained in the aqueous phase during the entire duration of the reaction. This implies an undesirable high salt load which must either be disposed of or recovered by tedious procedures after completion of the reaction. Furthermore, the epoxidation of exemplified alkenes containing more than one carbon-carbon double bond is not always selective only towards the target double bond, thus leading to the formation of relatively high amounts of undesired by-products.

Gan L.-H. et al, European Polymer Journal, Vol. 22, No. 7, pages 573-576, 1986 and Gnecco S. et al, Polymer Bulletin, Vol. 37, No. 5, pages 609-615, 1996 both describe the epoxidation of certain natural rubbers containing polyisoprene units by using performic acid generated "in situ" from formic acid and hydrogen peroxide. Likewise, the carbon-carbon double bonds in the polyisoprene backbone are not more than trisubstituted. Further, it is taught that the main problem of this epoxidation process is the formation of various secondary ring-opened and ring-expanded products, e.g. hydroxyls, esters (formate) and hydrofuran. However, relatively long reaction times and high ratios of hydrogen peroxide to formic acid are required to achieve a higher epoxidation level in the final product.

Patra A. et al, Organic Preparations and Procedures Int., Vol. 35, No. 5, pages 515-525, 2003 describes the epoxidation of the carbon-carbon double bonds of α, β-unsaturated carbonyl compounds (including a tetrasubstituted double bond, see compound 7) by using aqueous hydrogen peroxide in the presence of sodium ethoxide. In view of safety and economic concerns, the use of sodium ethoxide is undesirable due to its highly flammable and corrosive nature. Further, sodium ethoxide only dissolves in polar solvents such as ethanol. Polar solvents are somewhat expensive and difficult to regenerate. Water present in the polar solvents used may react with strong bases such as sodium ethoxide and decompose them.

In view of the above drawbacks, there is still need for improved methods for the epoxidation of tetrasubstituted alkenes, in particular terpinolene (Ia), which would not only make the process safe and environmentally friendly, but also would be simple and cost-effective for commercial utilization.

It is therefore an object of the present invention to overcome or ameliorate at least one of the above disadvantages and thus to provide an improved and more economically and commercially feasible process for the epoxidation of tetrasubstituted alkenes, in particular terpinolene (Ia).

Another object is to provide an industrially simple process for the epoxidation of tetrasubstituted alkenes, in particular terpinolene (Ia), which gives the corresponding epoxides, in particular terpinolene epoxide (IIa), in good yields.

A further object is to provide a more environmentally friendly process for the epoxidation of tetrasubstituted alkenes, in particular terpinolene (Ia), by reducing unfavorable environmental effects.

Still another object is to provide an industrially feasible process for the epoxidation of tetrasubstituted alkenes, in particular terpinolene (Ia), which reduces safety concerns and the existence of hazardous conditions.

Yet another object is to provide a process for the epoxidation of tetrasubstituted alkenes, in particular those containing at least one (preferably one or two and more preferably one) additional carbon-carbon double bond (the additional carbon-carbon double bond preferably being disubstituted or trisubstituted, more preferably trisubstituted) such as, for example, terpinolene (Ia) which results in a higher selectivity towards the epoxidation of the tetrasubstituted double bond while reducing the formation of undesirable by-products.

It has now surprisingly been found that these and further objects are, in part or in whole, achieved by a process for the epoxidation of a tetrasubstituted alkene to the corresponding epoxide comprising reacting the tetrasubstituted alkene with performic acid prepared in situ from formic acid and hydrogen peroxide in the presence of at least one buffering agent.

Accordingly, the aforementioned process for the epoxidation of a tetrasubstituted alkene is a subject matter of the present invention.

The process according to the present invention entails a series of advantages and overcomes drawbacks of the prior art processes.

The process of this invention avoids the handling of preformed peroxy acid solutions thus minimizing the risk of explosions while maintaining efficiency and ease of operations. The in-situ preparation of performic acid from formic acid and hydrogen peroxide allows the epoxidation of the tetrasubstituted alkene to proceed in a smooth and controlled manner, which is very safe, simple, economical, user-friendly and commercially viable.

Further, the process of this invention uses a relatively inexpensive starting material, i.e. formic acid, which is desirable from an economical point of view.

Formic acid can also easily be removed with an aqueous phase after completion of the epoxidation reaction and its use leads to a reduced TOC (Total Organic Carbon) content in the production wastewater in comparison with higher carboxylic acids as exemplified in the prior art processes. In addition, formic acid possesses an extremely good biodegradability which makes the process eco-friendly.

The process of this invention can be performed without any halogen-containing solvents and/or auxiliaries thus avoiding hazardous AOX compounds in the production wastewater, which is also desirable from an ecological point of view.

Another advantage of the process of this invention is that it is not required to maintain a high concentration of an inert and neutral inorganic salt (e.g. sodium sulfate, sodium chloride or potassium chloride) in the aqueous phase during the entire duration of the reaction. This avoids an undesirable high salt load to be disposed of or recovered after completion of the reaction, which makes the process eco-friendly as well.

Furthermore, the process of this invention provides the desired epoxide, in particular terpinolene epoxide (IIa), in high yields.

The process provides a very good selectivity towards the epoxidation of the tetrasubstituted double bond in tetrasubstituted alkenes containing at least one (preferably one or two and more preferably one) additional carbon-carbon double bond (the additional carbon-carbon double bond preferably being disubstituted or trisubstituted, more preferably trisubstituted), e.g. terpinolene (Ia). For example, a very good chemoselective epoxidation of the exocyclic double bond in terpinolene (Ia) can be achieved. Thus, undesired side reactions leading to unwanted by-products are minimized.

Accordingly, another subject matter of the present invention relates to the use of an oxidizing agent comprising hydrogen peroxide and formic acid for the in-situ epoxidation of a tetrasubstituted alkene, preferably a tetrasubstituted alkene containing at least one (preferably one or two and more preferably one) additional carbon-carbon double bond (the additional carbon-carbon double bond preferably being disubstituted or trisubstituted, more preferably trisubstituted), e.g. terpinolene (Ia).

Yet another subject matter of the present invention relates to the use of an oxidizing agent comprising hydrogen peroxide and formic acid for the selective in-situ epoxidation of a tetrasubstituted carbon-carbon double bond in a tetrasubstituted alkene, preferably a tetrasubstituted carbon-carbon double bond in a tetrasubstituted alkene containing at least one (preferably one or two and more preferably one) additional carbon-carbon double bond (the additional carbon-carbon double bond preferably being disubstituted or trisubstituted, more preferably trisubstituted) and in particular the exocyclic double bond in terpinolene (Ia).

The corresponding epoxide, in particular terpinolene epoxide (IIa), can also be easily isolated in high purity from the final reaction mixture by using conventional work-up procedures. The corresponding epoxide, in particular terpinolene epoxide (IIa), remains in the organic phase after phase separation whereas formic acid, peroxo compounds such as unreacted performic acid and hydrogen peroxide and salts predominantly enter the aqueous phase which can be subjected to waste water treatment. Small amounts of formic acid, peroxo compounds and salts still present in the organic phase can be removed by extractive work up and/or reduction of the peroxo compounds which contributes to a safely scalable process.

Any and all of these advantages make the process industrially simple, economical, safe and environmentally friendly.

Further embodiments of the invention are evident from the claims, the description and the examples. It is to be understood that the single features of the subject matter of the invention described herein can be applied not only in the combination given in each particular case but also in other combinations, without leaving the scope of the invention.

The starting materials according to the present invention are known compounds that are commercially available or can be prepared in a known manner.

The term "tetrasubstituted alkene" as used herein refers to an alkene having at least one carbon-carbon double bond wherein the carbon atoms of said double bond are bonded to a total of four carbon atoms excluding each other. The carbon-carbon double bond wherein the carbon atoms of said double bond are bonded to a total of four carbon atoms excluding each other is also referred to herein as "tetrasubstituted double bond".

Examples of such tetrasubstituted alkenes include but are not limited to 2,3-dimethyl-2-butene, 2,3,4-trimethyl-2-pentene, terpinolene of the formula (Ia), 1,2-dimethylcyclohexene, 5-cadinene, and taxadiene.

Preferably, the tetrasubstituted alkene is selected from tetrasubstituted alkenes containing at least one (preferably one or two and more preferably one) additional carbon-carbon double bond.

More preferably, the tetrasubstituted alkene is selected from tetrasubstituted alkenes containing at least one (preferably one or two and more preferably one) additional carbon-carbon double bond, the additional carbon-carbon double bond being disubstituted or trisubstituted.

Even more preferably, the tetrasubstituted alkene is selected from tetrasubstituted alkenes containing at least one (preferably one or two and more preferably one) additional carbon-carbon double bond, the additional carbon-carbon double bond being trisubstituted.

In particular, the tetrasubstituted alkene is selected from tetrasubstituted alkenes containing one additional carbon-carbon double bond, the additional carbon-carbon double bond being trisubstituted.

In another embodiment, the tetrasubstituted alkene is selected from an alkene of the formula (I)

(I)

wherein $R_1$, $R_2$, $R_3$ and $R_4$ are different from hydrogen and independently of one another represent a substituent selected from the group consisting of $C_1$-$C_6$-alkyl, $C_3$-$C_6$-cycloalkyl, $C_2$-$C_6$-alkenyl, $C_2$-$C_6$-alkynyl and $C_6$-$C_{20}$-aryl, or $R_1$ and $R_2$, or $R_1$ and $R_3$, or $R_2$ and $R_4$, or $R_3$ and $R_4$ in each case together represent a $C_2$-$C_{10}$-alkylene or $C_2$-$C_{10}$-alkenylene chain and form a 3-, 4-, 5-, 6-, 7-, 8-, 9-, 10-, 11- or 12-membered saturated or partially unsaturated monocyclic ring together with the one or two carbon atoms they are bonded to, wherein any one of the aforementioned substituents or $C_2$-$C_{10}$-alkylene or $C_2$-$C_{10}$-alkenylene chains may be substituted by one or more substituents each independently selected from the group consisting of halogen, $C_1$-$C_6$-alkyl and $C_1$-$C_6$-haloalkyl.

The organic moieties mentioned in the definition of the variables $R^1$, $R^2$, $R^3$ and $R^4$ are—like the term halogen—collective terms for individual enumerations of the individual group members. The term "halogen" denotes in each case fluorine, chlorine, bromine or iodine. All hydrocarbon chains, e.g. alkyl or alkenyl chains, can be straight-chain or branched, the prefix $C_n$-$C_m$ denoting in each case the possible number of carbon atoms in the group.

Examples of such meanings are:

$C_1$-$C_6$-alkyl: for example $CH_3$, $C_2H_5$, n-propyl, CH$(CH_3)_2$, n-butyl, $CH(CH_3)$—$C_2H_5$, $CH_2$—$CH(CH_3)_2$, $C(CH_3)_3$, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_3$-$C_6$-cycloalkyl: for example cyclopropyl, cyclobutyl, cyclopentyl and cyclohexyl;

$C_2$-$C_6$-alkenyl, for example, ethenyl, 1-propenyl, 2-propenyl, 1-methylethenyl 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl;

$C_2$-$C_6$-alkynyl: for example ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl or 1-ethyl-1-methyl-2-propynyl;

$C_2$-$C_{10}$-alkylene: a straight carbon chain having from 2 to 10 carbon atoms and having only carbon-carbon single bonds, for example ethylene ($CH_2CH_2$), n-propylene ($CH_2CH_2CH_2$), n-butylene ($CH_2CH_2CH_2CH_2$), n-pentylene ($CH_2CH_2CH_2CH_2CH_2$), n-hexylene (—$(CH_2)_6$—), n-heptylene (—$(CH_2)_7$—), n-octylene (—$(CH_2)_8$—), n-nonylene (—$(CH_2)_9$—) and n-decylene (—$(CH_2)_{10}$—);

$C_2$-$C_{10}$-alkenylene chain: a straight carbon chain having from 2 to 10 carbon atoms and at least one carbon-carbon double bond and no carbon-carbon triple bond, for example, CH=CH, CH=CH—$CH_2$, CH=CH—$CH_2CH_2$, CH=CH—CH=$CH_2$ and CH=CH—$CH_2CH_2CH_2$;

$C_1$-$C_6$-haloalkyl: a $C_1$-$C_6$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl.

The term "$C_6$-$C_{20}$-aryl" refers to an unsaturated aromatic carbocyclic group of from 6 to 20 carbon atoms having a single ring (e.g., phenyl) or multiple condensed (fused) rings, wherein at least one ring is aromatic (e.g. naphthalenyl or dihydrophenanthrenyl). Examples of $C_6$-$C_{20}$-aryls include phenyl, naphthalenyl, anthracenyl, indenyl or phenanthrenyl. A preferred aryl group is phenyl.

In another embodiment, the tetrasubstituted alkene is selected from terpenes, preferably cyclic terpenes, more preferably p-menthadienes and even more preferably terpinolene (Ia).

The term "terpenes" as used herein refers to natural substances constructed from isoprene basic units and derivatives. Depending on the number of basic units, terpene units are classified as monoterpenes, sesquiterpenes, diterpenes, sesterpenes, triterpenes, and tetraterpenes.

In another embodiment, the tetrasubstituted alkene is selected from cyclic terpenes comprising at least one (preferably one) exocyclic or endocyclic double bond, in particular at least one (preferably one) tetrasubstituted exocyclic or endocyclic double bond.

In another embodiment, the tetrasubstituted alkene is selected from cyclic terpenes comprising at least one (preferably one) exocyclic double bond, in particular at least one (preferably one) tetrasubstituted exocyclic double bond.

In another embodiment, the tetrasubstituted alkene is selected from cyclic terpenes comprising at least one (preferably one) endocyclic double bond, in particular at least one (preferably one) tetrasubstituted endocyclic double bond.

In another embodiment, the tetrasubstituted alkene is selected from cyclic terpenes comprising at least one (preferably one) exocyclic double bond, in particular at least one (preferably one) tetrasubstituted exocyclic double bond, and at least one (preferably one) endocyclic double bond, in particular at least one (preferably one) di- or trisubstituted (preferably trisubstituted) endocyclic double bond.

The term "exocyclic double bond" as used herein refers to a double bond between two carbon atoms wherein at least one carbon atom of the double bond is not constituent of the carbocyclic ring system. In one embodiment, the term "exocyclic double bond" refers to a double bond between two carbon atoms wherein one carbon atom of the double bond is not constituent of the carbocyclic ring system, while the other carbon atom of the double bond is constituent of the carbocyclic ring system. In another embodiment, the term "exocyclic double bond" refers to a double bond between two carbon atoms wherein both carbon atoms of the double bond are not constituent of the carbocyclic ring system.

The term "endocyclic double bond" as used herein refers to a double bond between two carbon atoms wherein both carbon atoms of the double bond are constituent of the carbocyclic ring system.

The terms "exocyclic double bond" and "endocyclic double bond" are further illustrated by the following scheme:

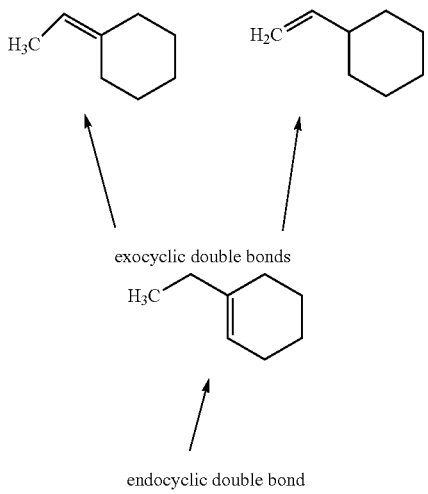

exocyclic double bonds endocyclic double bond

Most preferably, the tetrasubstituted alkene is terpinolene of the formula (Ia)

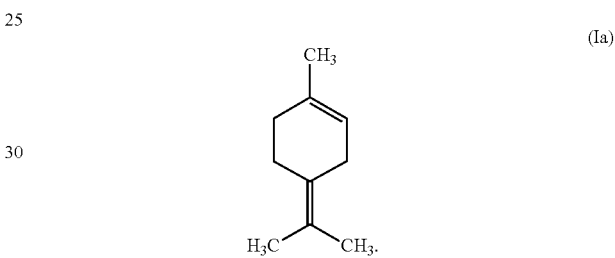

In another embodiment of this invention, the tetrasubstituted alkene is terpinolene of the formula (Ia) and the corresponding epoxide is terpinolene epoxide of formula (IIa)

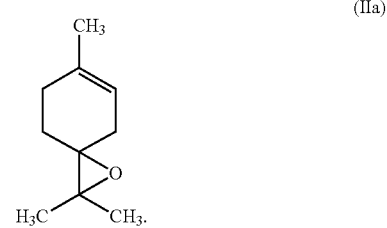

Thus, a particularly preferred embodiment of this invention relates to a process for the epoxidation of terpinolene of the formula (Ia) to terpinolene epoxide of formula (IIa) comprising reacting the terpinolene of the formula (Ia) with performic acid prepared in situ from formic acid and hydrogen peroxide in the presence of at least one buffering agent.

Other names of terpinolene (Ia) include p-Mentha-1,4(8)-diene, 1-Methyl-4-(1-methylethylidene)cyclohexene or 4-Isopropylidene-1-methylcyclohexene. Terpinolene used to be manufactured by fractional distillation of wood turpentine. It is now produced by treating alpha-pinene with aqueous phosphoric acid at 75° C. (see Eggersdorfer, M.; Terpenes. Ullmann's Encyclopedia of Industrial Chemistry. Vol. 36, 2012, Wiley-VCH Verlag, Weinheim).

The epoxidation of the tetrasubstituted alkene according to the present invention is carried out by reacting the tetrasubstituted alkene with performic acid prepared in situ from formic acid and hydrogen peroxide.

Formic acid can be used either as the pure material or as an aqueous solution, preferably one comprising at least 88% by weight, more preferably 95% by weight and even more preferably 98% by weight of formic acid.

Hydrogen peroxide can be used herein in all commercially available forms, for example, in the form of aqueous hydrogen peroxide solutions, as pure hydrogen peroxide, anhydrous hydrogen peroxide dissolved in organic solvents or in the form of compounds which are capable of releasing hydrogen peroxide under the reaction conditions (e.g. metal peroxides such as magnesium peroxide or zinc peroxide) as well as hydrogen peroxide adducts, such as, for example, urea hydrogen peroxide (also abbreviated as "UHP"). The most common form of urea hydrogen peroxide is the 1:1 molar adduct of urea and hydrogen peroxide ($CO(NH_2)_2 \ast H_2O_2$).

In a preferred embodiment, hydrogen peroxide is used as an aqueous solution, whereby the concentration of the solution is not critical. Preferably, the aqueous solution of hydrogen peroxide comprises at least 30% by weight and more preferably at least 50% by weight of hydrogen peroxide. Usually, the aqueous solution of hydrogen peroxide comprises 10% to 70% by weight, preferably 30 to 50% by weight of hydrogen peroxide.

The molar ratio of formic acid to the tetrasubstituted alkene, in particular terpinolene (Ia), can vary widely and depends on the reaction conditions used, but is generally from 0.1:1 to 2:1, preferably from 0.3:1 to 1.5:1, more preferably from 0.5:1 to 1.2:1 and even more preferably from 0.5:1 to 1:1.

The molar ratio of hydrogen peroxide to the tetrasubstituted alkene, in particular terpinolene (Ia), can likewise vary widely and depends on the reaction conditions used, but is generally from 0.4:1 to 2.5:1, preferably from 0.7:1 to 2:1, more preferably from 0.9:1 to 1.8: and even more preferably from 1:1 to 1.6:1.

The epoxidation of the tetrasubstituted alkene according to the present invention is carried out in the presence of at least one buffering agent.

It is preferable that the pH of the reaction mixture is maintained within a range of 1 to less than 7, more preferably within a range of 1 to 5, still more preferably within a range of 2 to 4 and even more preferably within a range of 2 to 3.

Thus, in a preferred embodiment, the buffering agent is capable of maintaining the pH of the reaction mixture within a range of 1 to less than 7, more preferably within a range of 1 to 5, still more preferably within a range of 2 to 4 and even more preferably within a range of 2 to 3.

In another preferred embodiment, the buffering agent is present in an amount sufficient to maintain the pH of the reaction mixture within a range of 1 to less than 7, more preferably within a range of 1 to 5, still more preferably within a range of 2 to 4 and even more preferably within a range of 2 to 3.

The molar ratio of the buffering agent to the tetrasubstituted alkene, in particular terpinolene (Ia), can vary and depends on the nature of the buffering agent and the reaction conditions used, but is generally from 0.1:1 to 2.5:1, preferably from 0.2:1 to 1.5:1, more preferably from 0.2:1 to 1:1 and even more preferably from 0.2:1 to 0.7:1.

Preferably, the buffering agent is selected from salts of inorganic acids, salts of organic acids and any combination thereof, more preferably selected from alkali metal and alkaline earth metal salts of inorganic acids, organic acids and any combination thereof.

The term "alkali metal" as used herein includes but is not limited to lithium, sodium and potassium.

The term "alkaline earth metal" as used herein includes but is not limited to calcium and magnesium.

More preferably, the buffering agent is a salt selected from phosphates, formates, acetates, carbonates, citrates, sulfates, cacodylates, fumarates, malates, tartrates and any combination thereof, even more preferably selected from phosphates, formates, acetates, carbonates, citrates, sulfates and any combination thereof and in particular selected from phosphates, formates and any combination thereof. Most preferably, the buffering agent is a salt selected from phosphates.

The term "phosphates" as used herein refers to salts comprising a phosphate ion ($PO_4^{3-}$), a hydrogen phosphate ion ($HPO_4^{2-}$), a dihydrogen phosphate ion ($H_2PO_4^{-}$), a diphosphate ion ($P_2O_7^{4-}$), a hydrogen diphosphate ion ($HP_2O_7^{3-}$), a dihydrogen diphosphate ion ($H_2P_2O_7^{2-}$), a polyphosphate ion ($P_nO_{3m+1}^{(n+2)-}$, wherein n is an integer greater than or equal to 3) such as, for example, a triphosphate ion ($P_3O_{10}^{5-}$) or a tetraphosphate ion ($P_4O_{14}^{6-}$), or a cyclic metaphosphate ion ($(PO_3^{-})_n$ wherein n is an integer greater than or equal to 3) such as, for example, a cyclic trimetaphosphate ion ($P_3O_9^{3-}$).

The term "formates" as used herein refers to salts derived from formic acid, i.e. salts comprising the formate or methanoate ion ($HCOO^{-}$).

The term "acetates" as used herein refers to salts derived from acetic acid, i.e. salts comprising the acetate or ethanoate ion ($CH_3COO^{-}$).

The term "carbonates" as used herein refers to salts comprising the carbonate ion ($CO_3^{2-}$) or hydrogen carbonate ion ($HCO_3^{-}$).

The term "citrates" as used herein refers to salts derived from citric acid, i.e. salts comprising the citrate ion ($C_3H_5O(COO)_3^{3-}$).

The term "cacodylates" as used herein refers to salts derived from cacodylic acid, i.e. salts comprising the cacodylate ion ($(CH_3)_2AsO^{2-}$).

The term "fumarates" as used herein refers to salts derived from fumaric acid, i.e. salts comprising the fumarate dianion (—OOC—CH=CH—COO$^{-}$).

The term "malates" as used herein refers to salts derived from malic acid, i.e. salts comprising the malate dianion (—OOC—CH$_2$—CH(OH)—COO$^{-}$).

The term "tartrates" as used herein refers to salts derived from tartaric acid, i.e. salts comprising the tartrate dianion (—OOC—CH(OH)—CH(OH)—COO—).

The term "sulfates" as used herein refers to salts derived from sulfuric acid, i.e. salts comprising the sulfate ion ($SO_4^{2-}$).

More preferably, the buffering agent is selected from alkali metal and alkaline earth metal phosphates, alkali metal and alkaline earth metal formates, alkali metal and alkaline earth metal acetates, alkali metal and alkaline earth metal carbonates, alkali metal and alkaline earth metal citrates, alkali metal and alkaline earth metal sulfates and any combination thereof, even more preferably selected from alkali metal and alkaline earth metal phosphates, alkali metal and alkaline earth metal formates, alkali metal and alkaline earth metal acetates, alkali metal and alkaline earth metal carbonates, alkali metal and alkaline earth metal citrates and any combination thereof, in particular selected from alkali metal and alkaline earth metal phosphates, alkali metal and alkaline earth metal formates and any combination thereof, most preferably selected from alkali metal phosphates, alkali metal formates and any combination thereof.

In another embodiment, the buffering agent is selected from alkali metal and alkaline earth metal phosphates, preferably alkali metal phosphates.

In another embodiment, the buffering agent is selected from di-(alkali metal) hydrogen phosphates, alkali metal dihydrogen phosphates, alkali metal formates, alkali metal acetates, alkali metal hydrogen carbonates, alkali metal citrates, alkali metal sulfates and any combination thereof, preferably from di-(alkali metal) hydrogen phosphates, alkali metal formates and any combination thereof. Most preferably, the buffering agent is selected from di-(alkali metal) hydrogen phosphates.

In another embodiment, the buffering agent is selected from lithium phosphate, sodium phosphate, potassium phosphate, calcium phosphate, magnesium phosphate, dilithium hydrogen phosphate, disodium hydrogen phosphate, dipotassium hydrogen phosphate, calcium hydrogen phosphate, magnesium hydrogen phosphate, lithium dihydrogen phosphate, sodium dihydrogen phosphate, potassium dihydrogen phosphate, calcium dihydrogen phosphate, magnesium dihydrogen phosphate, lithium formate, sodium formate, potassium formate, calcium formate, magnesium formate, lithium acetate, sodium acetate, potassium acetate, calcium acetate, magnesium acetate, lithium carbonate, sodium carbonate, potassium carbonate, calcium carbonate, magnesium carbonate, lithium hydrogen carbonate, sodium hydrogen carbonate, potassium hydrogen carbonate, calcium hydrogen carbonate, magnesium hydrogen carbonate, lithium citrate, sodium citrate, potassium citrate, calcium citrate, magnesium citrate, lithium sulfate, sodium sulfate, potassium sulfate, calcium sulfate, magnesium sulfate and any combination thereof.

More preferably, the buffering agent is selected from disodium hydrogen phosphate, dipotassium hydrogen phosphate, sodium dihydrogen phosphate, potassium dihydrogen phosphate, sodium formate, potassium formate, lithium acetate, sodium acetate, potassium acetate, calcium acetate, magnesium acetate, calcium carbonate, sodium hydrogen carbonate, potassium hydrogen carbonate, sodium citrate, potassium citrate, lithium sulfate, sodium sulfate, potassium sulfate, calcium sulfate, magnesium sulfate and any combination thereof.

Even more preferably, the buffering agent is selected from disodium hydrogen phosphate, dipotassium hydrogen phosphate, sodium dihydrogen phosphate, potassium dihydrogen phosphate, sodium formate, potassium formate, sodium acetate, potassium acetate, sodium hydrogen carbonate, potassium hydrogen carbonate, sodium citrate, potassium citrate, sodium sulfate, potassium sulfate and any combination thereof.

In particular, the buffering agent is selected from disodium hydrogen phosphate, sodium formate and any combination thereof. Most preferably, the buffering agent is disodium hydrogen phosphate.

In a preferred embodiment, the process of this invention is carried out in the presence of at least one inert organic solvent By "inert organic solvent" is meant an organic solvent which, under the reaction conditions of the process of this invention, does not enter into any appreciable reaction with either the reactants or the products.

In another embodiment, the process of this invention is carried out in the absence of at least one inert organic solvent.

In another embodiment, the inert organic solvent is selected from non-halogenated inert organic solvents.

The inert organic solvent used in the process of this invention is preferably selected from non-halogenated aliphatic hydrocarbons, non-halogenated cycloaliphatic hydrocarbons, non-halogenated aromatic hydrocarbons, halogenated aliphatic hydrocarbons, halogenated aromatic hydrocarbons, amides, ethers, esters, ketones, nitriles and any combination thereof.

Examples of suitable non-halogenated aliphatic hydrocarbons include pentane, hexane, heptane, and the like. Preference is given to saturated aliphatic hydrocarbons having from 5 to 10 carbon atoms.

Examples of suitable non-halogenated cycloaliphatic hydrocarbons include cyclopentane, cyclohexane, cycloheptane, and the like. Preference is given to non-halogenated saturated cycloaliphatic hydrocarbons having from 5 to 10 carbon atoms. Cyclohexane is particularly preferred.

Examples of suitable a non-halogenated aromatic hydrocarbons include toluene, o-xylene, m-xylene, p-xylene, ethylbenzene, 2-propylbenzene (cumene), 2-isopropyltoluene (o-cymol), 3-isopropyltoluene (m-cymol), 4-isopropyltoluene (p-cymol), 1,3,5-trimethylbenzene (mesitylene), and the like. Preference is given to toluene, o-xylene, m-xylene, p-xylene, ethylbenzene, 1,3,5-trimethylbenzene (mesitylene), and any combination thereof. Especially preferred among the non-halogenated aromatic hydrocarbons are toluene, o-xylene, m-xylene, p-xylene, and any combination thereof, with toluene being the most preferred.

Examples of suitable halogenated aliphatic hydrocarbons include methylene chloride, chloroform, carbon tetrachloride, 1,2-dichloroethane, 1,1,1,2-tetrachloroethane, 1,1,2,2-tetrachloroethane, 1,1-dichloroethylene, 1,2-dichloroethylene, and the like. Preference is given to methylene chloride and 1,2-dichloroethane and any combination thereof.

Examples of suitable halogenated aromatic hydrocarbons include chlorobenzene, bromobenzene, o-dichlorobenzene, m-dichlorobenzene, α,α,α-trifluorotoluene (benzotrifluoride) and the like.

Examples of suitable amides include N,N-dimethylformamide, dimethylacetamide, diethylacetamide, and the like.

Examples of suitable ethers include cyclic and acyclic ethers such as diethyl ether, diisopropyl ether, n-butyl methyl ether, isobutyl methyl ether, sec-butyl methyl ether, tert-butyl methyl ether, cyclopentyl methyl ether, tetrahydrofuran, 1,4-dioxane, and the like.

Examples of suitable esters include ethyl acetate, n-propylacetate, isopropyl acetate, tert-butyl acetate, and the like.

Examples of suitable ketones include acetone, methyl ethyl ketone, methyl isopropyl ketone, methyl isobutyl ketone, cyclopropyl methyl ketone and the like.

Examples of suitable nitriles include acetonitrile, benzonitrile, and the like.

In a preferred embodiment, the inert organic solvent is selected from non-halogenated aliphatic hydrocarbons, non-halogenated aromatic hydrocarbons, halogenated aliphatic hydrocarbons, ethers, halogenated aromatic hydrocarbons and any combination thereof.

In a more preferred embodiment, the inert organic solvent is selected from heptane, toluene, o-xylene, m-xylene, p-xylene, ethylbenzene, 1,3,5-trimethylbenzene (mesitylene), methylene chloride, tert-butyl methyl ether and any combination thereof.

In an even more preferred embodiment, the inert organic solvent is selected from heptane, toluene, methylene chloride, tert-butyl methyl ether and any combination thereof.

In another embodiment, the inert organic solvent is selected from non-halogenated hydrocarbons, preferably from non-halogenated aliphatic hydrocarbons, non-halogenated cycloaliphatic hydrocarbons, non-halogenated aromatic hydrocarbons and any combination thereof, more preferably from heptane, cyclohexane, cycloheptane, toluene, o-xylene, m-xylene, p-xylene, ethylbenzene, 1,3,5-trimethylbenzene (mesitylene) and any combination thereof.

Still more preferably, the inert organic solvent is selected from heptane, toluene, tert-butyl methyl ether and any combination thereof.

Particularly preferred inert organic solvents are non-halogenated aromatic hydrocarbons, especially non-halogenated alkylbenzenes which are mono-, di-, or trialkylsubstituted with each alkyl group containing 1 to 3 carbon atoms, and in particular those selected from the group consisting of toluene, o-xylene, m-xylene, p-xylene, and any combination thereof. Most preferably, the inert organic solvent is toluene.

The volume ratio of the inert organic solvent to the tetrasubstituted alkene, in particular terpinolene (Ia), is generally from 0.01:1 to 20:1, preferably from 0.1:1 to 15:1, more preferably from 0.5:1 to 10:1, and most preferably from 1:1 to 5:1.

The process of the present invention can be carried out under atmospheric pressure or under slightly elevated or reduced pressure. Typically, the atmospheric pressure is employed.

The temperature used in the process of the present invention can vary widely and is preferably from 0 to 70° C., more preferably from 5 to 60° C. and even more preferably from 10 to 50° C.

The reaction time can vary in a wide range and depends on a variety of factors such as, for example, temperature, pressure, or the reagents and auxiliary substances used. Typical reaction times are in the range of from 1 to 20 hours, preferably from 2 to 15 hours and more preferably from 3 to 10 hours.

In a preferred embodiment, the reaction of the tetrasubstituted alkene (in particular terpinolene (Ia)) with performic acid prepared in situ from formic acid and hydrogen peroxide comprises the steps of
(a) Providing a first mixture comprising the tetrasubstituted alkene (in particular terpinolene (Ia)), formic acid, the buffering agent and optionally the inert organic solvent,
(b) Adding hydrogen peroxide to the first mixture under agitation to form a second mixture, and
(c) Agitating the second mixture.

In another embodiment, step (a) is carried out by following the steps of
(a1) Providing a mixture comprising the tetrasubstituted alkene (in particular terpinolene (Ia)), the buffering agent and optionally the inert organic solvent, and
(a2) adding formic acid to the mixture obtained from step (a1) to give the first mixture.

Step (a) is preferably carried out at a temperature of 0 to 30° C., more preferably 0 to 20° C.

In step (b), hydrogen peroxide is preferably added under agitation to the first mixture at a temperature of 10 to 70° C., more preferably 20 to 60° C. and even more preferably 30 to 60° C.

In step (b), hydrogen peroxide is preferably added under agitation to the first mixture over a period of at least 10 minutes, more preferably at least 1 hour, even more preferably at least 3 hours and in particular from 3 to 8 hours.

Preferably, hydrogen peroxide is added under agitation to the first mixture at a temperature of at least 20° C., more preferably at least 30° C. and in particular 30 to 60° C. over a period of at least 3 hours (in particular 3 to 8 hours). Any and all these measures are predominantly intended to prevent accumulation of the explosive performic acid in the reaction mixture.

In another embodiment, a stabilizing agent can be employed in the peroxy-containing reaction mixture. Such stabilizers are well known and are, for example, urea, pyridine N-oxide, 2,3-pyridine-dicarboxylic acid, 2,6-pyridinedicarboxylic acid, phosphates, diphosphates, polyphosphates, metaphosphates, ethylenediaminetetraacetic acid (EDTA) and any combination thereof.

The stabilizing agent should be present in the reaction mixture in an amount of 0.1 to 10% by weight of the reaction mixture.

In another embodiment, an organic radical scavenger may be present in the reaction mixture. Non limiting examples of organic radical scavengers include phenols such as, for example, hydroquinone, monomethylhydroquinone, 2,6-Bis (1,1-dimethylethyl)-4-methylphenol (BHT) and any combination thereof. The organic radical scavenger may be used in an amount of 0.01 to 10% by weight of the reaction mixture.

Step (c) is preferably carried out at a temperature of 0 to 30° C., more preferably 0 to 20° C.

In another embodiment, a higher temperature is used in step (b) than in step (c). Preferably, the temperature in step (b) is from 30 to 60° C. and the temperature in step (c) is from 0 to 20° C.

The corresponding epoxide (in particular terpinolene epoxide (IIa)) is preferably isolated from the final reaction mixture obtained in step (c) by employing conventional methods, for example by extraction, in particular extraction with a basic or neutral aqueous medium, distillation, and the like.

In another embodiment, excess peroxo compounds present in the final reaction mixture are reduced before or after work up of the reaction mixture. The term "excess peroxo compounds" as used herein includes unreacted performic acid and/or unreacted hydrogen peroxide still present in the final reaction mixture obtained after completion or partial completion of the reaction. Preferably, the final reaction mixture or the organic phase separated from the final reaction mixture is treated with at least one reducing agent. Any suitable reducing agent may be employed in carrying out the process of this invention, however, it is preferred to employ a reducing agent selected from alkali metal sulfites, thiosulfates, alkaline earth metal sulfites, sulfur dioxide, formaldehyde, para-formaldehyde and any combination thereof, more preferably from alkali metal sulfites, in particular sodium sulfite ($Na_2SO_3$), potassium sulfite ($K_2SO_3$) or a combination thereof. The reducing agent may be used in pure form or as an aqueous solution, preferably as an aqueous solution. For example, an aqueous solution comprising 10 to 45% by weight of an alkali metal sulfite, in particular sodium sulfite ($Na_2SO_3$), potassium sulfite ($K_2SO_3$) or a combination thereof is employed as the reducing agent.

In another embodiment, the process of this invention further comprises separating the final reaction mixture into an aqueous phase and an organic phase and removing excess amounts of formic acid, performic acid and hydrogen peroxide from the organic phase by aqueous extraction, in particular with water or with an aqueous base solution. Suitable bases employed in the aqueous base solution include but are not limited to alkali metal and alkaline earth metal hydroxides, alkali metal and alkaline earth metal carbonates, alkali metal and alkaline earth metal hydrogen carbonates or any combination thereof, preferably alkali metal hydroxides, in particular sodium hydroxide, potassium hydroxide or a combination thereof. For example, an aqueous solution comprising 1 to 20% by weight of an alkali metal hydroxide, in particular sodium hydroxide, potassium hydroxide or a combination thereof is employed for the aqueous extraction.

In another embodiment, the final reaction mixture is distilled to obtain the corresponding epoxide (in particular terpinolene epoxide (IIa)), optionally the inert solvent and a residue. Further, the organic phase obtained from phase separation of the final reaction mixture can also be subjected to distillation.

In another embodiment, the tetrasubstituted alkene (in particular terpinolene (Ia)) is partially converted to the corresponding epoxide (in particular terpinolene epoxide (IIa)) and recycled, preferably to step (a) or more specifically to step (a1). Such partial conversion is particularly advantageous for increasing the selectivity towards the epoxidation of the tetrasubstituted double bond in tetrasubstituted alkenes containing at least one (preferably one or two and more preferably one) additional carbon-carbon double bond (the additional carbon-carbon double bond preferably being disubstituted or trisubstituted, more preferably trisubstituted), e.g. terpinolene (Ia). For this purpose, the tetrasubstituted alkene (in particular terpinolene (Ia)) is isolated from the reaction mixture after partial completion of the reaction by using any or all the aforementioned work-up procedures in an analogous manner, in particular phase separation, aqueous extraction of the organic phase, reductive treatment of the reaction mixture obtained after partial completion of the reaction or of the organic phase obtained from phase separation in order to remove excess amounts of peroxo compounds and distillation of the reaction mixture obtained after partial completion of the reaction or of the organic phase obtained from phase separation to separate the corresponding epoxide (in particular terpinolene epoxide (IIa), unreacted tetrasubstituted alkene (in particular unreacted terpinolene (Ia)) and by-products. The fraction of the unreacted tetrasubstituted alkene (in particular unreacted terpinolene (Ia)) can be recycled to a new epoxidation reaction, and the fraction of the corresponding epoxide (in particular terpinolene epoxide (IIa)) can be forwarded to a subsequent reaction step.

In another embodiment, terpinolene epoxide of formula (IIa) is further converted to limonene-4-ol.

In another embodiment, terpinolene epoxide of formula (IIa) is further converted to terpinene-4-ol.

Preferably, terpinolene epoxide of formula (IIa) is further converted via limonene-4-ol to terpinene-4-ol.

For example, terpinolene epoxide of formula (IIa) can be further subjected to an epoxide ring opening isomerization leading to limonene-4-ol, optionally followed by conventional hydrogenation to give terpinene-4-ol, as described, for example in GB 1 307 053.

Terpinene-4-ol can in turn be used as a starting material for the synthesis of oxabicycloalkane herbicides, in particular of (±)-2-exo-(2-Methylbenzyloxy)-1-methyl-4-isopropyl-7-oxabicyclo[2.2.1]heptane as described, for example in U.S. Pat. Nos. 4,487,945 or 4,542,244.

(±)-2-exo-(2-Methylbenzyloxy)-1-methyl-4-isopropyl-7-oxabicyclo[2.2.1]heptane (herein also referred to as the "exo-(±)-isomers", CAS RN 87818-31-3)

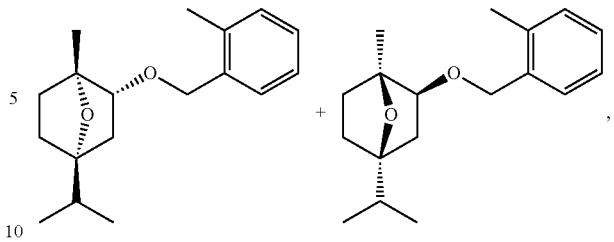

is the racemic mixture containing equal parts of the two enantiomers (+)-2-exo-(2-Methylbenzyloxy)-1-methyl-4-isopropyl-7-oxabicyclo[2.2.1]heptane (herein also referred to as the "exo-(+)isomer", CAS RN 87818-61-9) and (−)-2-exo-(2-Methylbenzyloxy)-1-methyl-4-isopropyl-7-oxabicyclo[2.2.1]heptane (herein also referred to as the "exo-(−)-isomer", CAS RN 87819-60-1). The exo-(±)-isomers, the exo-(+)-isomer and the exo-(−)-isomer including their preparation and herbicidal properties are disclosed in EP 0 081 893 A2 (see Examples 29, 34, 35 and 62). Further preparation methods of these compounds are described in U.S. Pat. No. 4,487,945 (see Embodiments 46 and 48). The racemic mixture (±)-2-exo-(2-Methylbenzyloxy)-1-methyl-4-isopropyl-7-oxabicyclo[2.2.1]heptane is also described in the The Pesticide Manual, Fourteenth Edition, Editor: C. D. S. Tomlin, British Crop Production Council, 2006, entry 157, pages 195-196 with its common name cinmethylin, its IUPAC name (1RS,2SR,4SR)-1,4-epoxy-p-menth-2-yl 2-methylbenzyl ether and its Chemical Abstracts name exo-(±)-1-methyl-4-(1-methylethyl)-2-[(2-methylphenyl) methoxy]-7-oxabicyclo[2.2.1]heptane.

Any of terpinolene epoxide of formula (IIa), limonene-4-ol and terpinene-4-ol are valuable intermediates in the preparation of (±)-2-exo-(2-Methylbenzyloxy)-1-methyl-4-isopropyl-7-oxabicyclo[2.2.1]heptane, any of its individual enantiomers or any non-racemic mixture thereof.

Any of terpinolene epoxide of formula (IIa), limonene-4-ol and terpinene-4-ol may be further converted into (±)-2-exo-(2-Methylbenzyloxy)-1-methyl-4-isopropyl-7-oxabicyclo[2.2.1]heptane, any of its individual enantiomers or any non-racemic mixture thereof. Further conversion into (±)-2-exo-(2-Methylbenzyloxy)-1-methyl-4-isopropyl-7-oxabicyclo[2.2.1]heptane, any of its individual enantiomers or any non-racemic mixture thereof can be accomplished by methods known in the art such as, for example, those described in EP 0 081 893 A2 and U.S. Pat. No. 4,487,945.

Thus, in a further aspect of the present invention, there is provided a process for preparing (±)-2-exo-(2-Methylbenzyloxy)-1-methyl-4-isopropyl-7-oxabicyclo[2.2.1]heptane, any of its individual enantiomers or any non-racemic mixture thereof comprising the steps of:

(i) preparing terpinolene epoxide of formula (IIa) (preferably limonene-4-ol, more preferably terpinene-4-ol) as described herein, and (ii) converting terpinolene epoxide of formula (IIa) (preferably limonene-4-ol, more preferably terpinene-4-ol) into (±)-2-exo-(2-Methylbenzyloxy)-1-methyl-4-isopropyl-7-oxabicyclo[2.2.1]heptane, any of its individual enantiomers or any non-racemic mixture thereof.

The invention is illustrated by the following examples without being limited thereto or thereby.

EXAMPLE 1: EPOXIDATION OF TERPINOLENE IN TOLUENE USING DISODIUM HYDROGEN PHOSPHATE (NA$_2$HPO$_4$) AS BUFFERING AGENT 600 g (4.141 mol) terpinolene (94% w/w) were dissolved in 1200 g toluene in a 4000 ml glass reactor. 240 g (1.673 mol) Na$_2$HPO$_4$ (99% w/w) were added in solid form at room temperature. 200 g (4.348 mol) formic acid (100% w/w) were slowly added at 10-15° C. under stirring (start pH: 2.15) before 425 g (6.25 mol) hydrogen peroxide (50% w/w) were dosed in over 6 h at 30° C. (end pH: 2.98). The mixture was stirred over 8 h at 17-18° C.

Phases were separated. 600 ml aqueous K$_2$SO$_3$ solution (20% w/w) were added to the organic phase under stirring for peroxide reduction. Phases were separated and the organic phase was extracted with 600 ml aqueous NaOH solution (10%). Finally the organic phase was extracted twice with each 600 ml demineralized water and a sample for quantitative GC analysis was taken: a content of 27.5% terpinolene epoxide equal to a yield of 79.8% was determined.

The organic phase was concentrated (evaporation of toluene) and the distillation sump was distilled over a short column for product purification.

EXAMPLE 2: EPOXIDATION OF TERPINOLENE IN TOLUENE USING SODIUM FORMATE (NAOOCH) AS BUFFERING AGENT 146.8 g (1.013 mol) terpinolene (94% w/w) were dissolved in 300 g toluene in a 1000 ml glass reactor. 28.4 g (0.405 mol) sodium formate (97% w/w) were added in solid form at room temperature. 47.1 g (1.013 mol) formic acid (99% w/w) were slowly added at <20° C. under stirring before 103.3 g (1.519 mol) hydrogen peroxide (50% w/w) were dosed in over 4 h at 40° C. The mixture was stirred over 8 h at 17° C.

Phases were separated. 150 ml aqueous K$_2$SO$_3$ solution (20% w/w) were added to the organic phase under stirring for peroxide reduction. Phases were separated and the organic phase was extracted with 150 ml aqueous NaOH solution (10%). Finally the organic phase was extracted with 150 ml demineralized water and a sample for quantitative GC (gas chromatography) analysis was taken: a content of 23.4% terpinolene epoxide equal to a yield of 71.0% was determined.

EXAMPLE 3: EPOXIDATION OF TERPINOLENE WITHOUT AN INERT ORGANIC SOLVENT 10 g (0.071 mol) terpinolene (96% w/w) and 3 g (0.043 mol) sodium formate (97% w/w) were mixed at 10-15° C. in a 100 ml glass reactor. 3.3 g (0.072 mol) formic acid (99% w/w) were slowly added at <15° C. under stirring before 7.5 g (0.110 mol) hydrogen peroxide (50% w/w) were dosed in over 15 min at <17° C. The mixture was stirred over 2 h at 15° C., 15 h at 0° C. and 8 h at 10° C. and a sample for HPLC analysis was taken. Product terpinolene epoxide: 69 area-%, starting material terpinolene: 5 area-%.

EXAMPLE 4: EPOXIDATION OF TERPINOLENE IN TOLUENE WITH PARTIAL CONVERSION 650 g (4.295 mol) terpinolene (90% w/w) was dissolved in 925 g toluene in a 4000 ml glass reactor. 110 g (1.569 mol) sodium formate (97% w/w) were added in solid form at room temperature. 400 g (4.348 mol) formic acid (100% w/w) were slowly added at <20° C. under stirring before 240 g (3.529 mol) hydrogen peroxide (50% w/w) were dosed in over 3 h at 30° C. The mixture was stirred over 17 h at 0° C. and a sample for HPLC analysis was taken. Product terpinolene epoxide: 54 area-%, starting material terpinolene: 36 area-%. Work up was performed similar to example 1. The terpinolene fraction was recycled to a new epoxidation experiment, the terpinolene epoxide forwarded to the next reaction step.

EXAMPLE 5: EPOXIDATION OF TERPINOLENE IN TOLUENE USING DISODIUM HYDROGEN PHOSPHATE (NA$_2$HPO$_4$) AS BUFFERING AGENT 895.4 g (6.00 mol) terpinolene (91.3% w/w), 1105.8 g (12.00 mol) toluene and 301.26 g (2.10 mol) Na$_2$HPO$_4$ (99% w/w) were placed in a glass reactor at 20° C. 279.01 g (6.00 mol) formic acid (99% w/w) were slowly added over 15 minutes under stirring and reaction mixture was heated to 35° C. Then 572.96 g (8.40 mol) hydrogen peroxide (50% w/w) were dosed continuously over 5 h at 35° C. to the reaction mixture under stirring. The reaction mixture was stirred for further 3 h at 35° C.

Water phase was separated and disposed. Then reaction mixture was cooled to 20° C. To the organic phase in the reactor were added 622 g (1.555 mol) sodium hydroxide solution (10% in water) over 30 minutes at 20° C. and mixture was stirred for 1 h at 20° C. Phases were separated.

The lower aqueous phase was disposed. To the organic phase in the reactor were added 622 g demineralized water and mixture was stirred for 1 h at 20° C. Phases were separated.

Organic product phase: 2082.3 g.

A sample for quantitative GC analysis was taken: a content of 35.17% terpinolene epoxide equal to a yield of 80.2% was determined.

COMPARATIVE EXAMPLE 1 (ANALOGOUS TO EP 0032990 A1): EPOXIDATION OF TERPINOLENE IN TOLUENE USING SODIUM FORMATE (NAOOCH) AND ANHYDROUS SODIUM SULFATE AS BUFFERING AGENTS 149.2 g (1.00 mol) terpinolene (91.3% w/w), 184.3 g (2.00 mol) toluene, 12.1 g (0.084 mol) anhydrous sodium sulfate (Na$_2$SO$_4$, 99% w/w) and 7.9 g (0.112 mol) sodium formate (NaOOCH, 97% w/w) were placed in a glass reactor at 20° C. 46.5 g (1.00 mol) formic acid (99% w/w) were slowly added over 15 minutes under stirring and reaction mixture was heated to 35° C. Then 95.5 g (1.4 mol) hydrogen peroxide (50% w/w) were dosed continuously over 5 h at 35° C. to the reaction mixture under stirring. The reaction mixture was stirred for further 3 h at 35° C.

Water phase was separated and disposed. Then reaction mixture was cooled to 20° C. To the organic phase in the reactor were added 104 g (0.26 mol) sodium hydroxide solution (10% in water) over 30 minutes at 20° C. and mixture was stirred for 1 h at 20° C. Phases were separated. The lower aqueous phase was disposed. To the organic phase in the reactor were added 103.7 g demineralized water and mixture was stirred for 1 h at 20° C. Phases were separated.

Organic product phase: 322.3 g.

A sample for quantitative GC analysis was taken: a content of 11.0% terpinolene epoxide equal to a yield of 23.3% was determined.

The invention claimed is:

1. A process for the epoxidation of a tetrasubstituted alkene to the corresponding epoxide comprising reacting the tetrasubstituted alkene with performic acid prepared in situ from formic acid and hydrogen peroxide in the presence of at least one buffering agent
wherein the tetrasubstituted alkene is terpinolene of the formula (Ia)

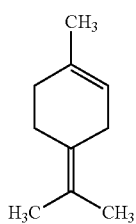

(Ia)

and the corresponding epoxide is terpinolene epoxide of formula (IIa)

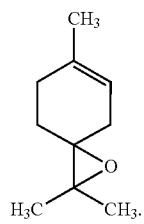

(IIa)

2. The process according to claim 1 wherein the buffering agent is selected from salts of inorganic acids, salts of organic acids and any combination thereof.

3. The process according to claim 1 wherein the buffering agent is a salt selected from phosphates, formates, acetates, carbonates, citrates, sulfates and any combination thereof.

4. The process according to claim 1 wherein the buffering agent is selected from alkali metal and alkaline earth metal phosphates, alkali metal and alkaline earth metal formates and any combination thereof.

5. The process according to claim 1 wherein the buffering agent is selected from alkali metal phosphates.

6. The process according to claim 1 wherein the buffering agent is selected from di-(alkali metal) hydrogen phosphates.

7. The process according to claim 1 wherein the reaction is carried out in the presence of at least one inert organic solvent.

8. The process according to claim 7 wherein the inert organic solvent is selected from non-halogenated aliphatic hydrocarbons, non-halogenated cycloaliphatic hydrocarbons, non-halogenated aromatic hydrocarbons, halogenated aliphatic hydrocarbons, halogenated aromatic hydrocarbons, amides, ethers, esters, ketones, nitriles and any combination thereof.

9. The process according to claim 7 wherein the inert organic solvent is selected from non-halogenated inert organic solvents.

10. The process according to claim 1 wherein the temperature is from 0 to 70° C.

11. The process according to claim 1 wherein the terpinolene epoxide of formula (IIa) is further converted via limonene-4-ol to terpinene-4-ol.

12. The process according to claim 1, wherein the terpinolene epoxide of formula (IIa), limonene-4-ol or terpinene-4-ol is further converted into (±)-2-exo-(2-Methylbenzyloxy)-1-methyl-4-isopropyl-7-oxabicyclo[2.2.1]heptane, any of its individual enantiomers or any non-racemic mixture thereof.

* * * * *